Figure 1:
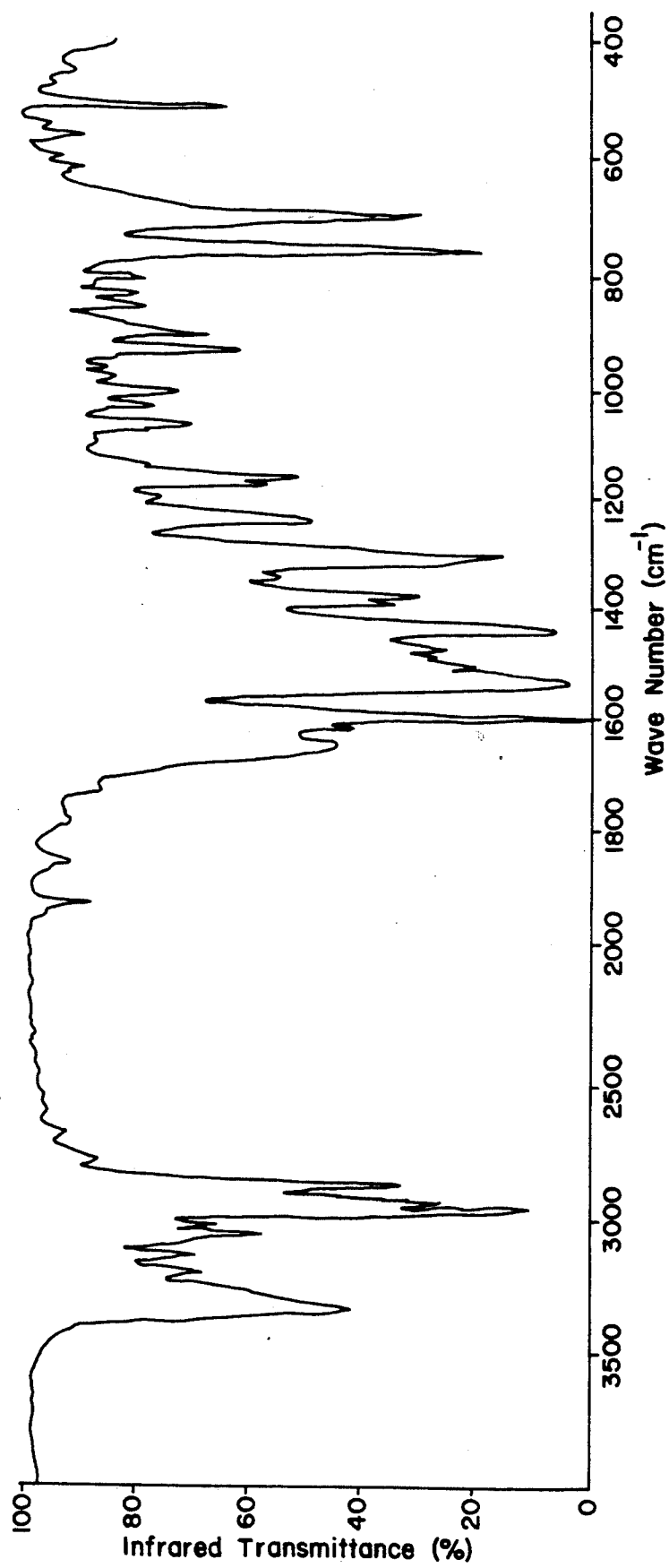

United States Patent [19]

Steltenkamp

[11] Patent Number: 5,182,305
[45] Date of Patent: Jan. 26, 1993

[54] N-ARYL AND N-CYCLOAKYL NEOALKANAMIDE INSECT REPELLENTS

[75] Inventor: Robert J. Steltenkamp, Somerset, N.J.

[73] Assignee: Colgate-Palmolive Co., New York, N.Y.

[21] Appl. No.: 657,707

[22] Filed: Feb. 19, 1991

Related U.S. Application Data

[63] Continuation-in-part of Ser. No. 612,747, Nov. 12, 1990, and a continuation-in-part of Ser. No. 267,141, Nov. 4, 1988, Pat. No. 5,006,562, and a continuation-in-part of Ser. No. 609,290, Nov. 5, 1990, and a continuation-in-part of Ser. No. 264,936, Oct. 31, 1988, Pat. No. 5,015,665, and a continuation-in-part of Ser. No. 894,985, Aug. 8, 1986, abandoned.

[51] Int. Cl.$^5$ ............................................. A01N 37/18
[52] U.S. Cl. ...................................... 514/629; 514/919
[58] Field of Search ................ 564/217, 218; 514/629, 514/919

[56] References Cited

U.S. PATENT DOCUMENTS 2,891,912  6/1959  Schwartz ............................ 252/152
3,852,058 12/1974  Huffman ......................... 564/218 X
4,804,683  2/1989  Steltenkamp ........................ 514/629

OTHER PUBLICATIONS

Chemical Abstracts 83:77944g (Ramana et al) 1975.

Primary Examiner—Leonard Schenkman
Attorney, Agent, or Firm—Bernard Lieberman; Robert C. Sullivan

[57] ABSTRACT

N-monosubstituted neoalkanamides of 11 to 14 carbon atoms wherein the substituent on the amide nitrogen is cyclic (aromatic or cycloaliphatic, such as aryl or cycloalkyl) and of at least five carbon atoms, have been discovered to be insect repellent, providing that any aromatic substituent is unsubstituted at the ortho position and that when the neoalkanoyl moiety is pivaloyl the total number of carbon atoms in the N-cyclic neoalkanamide is at least 12. Such neoalkanamides are useful as repellents against cockroaches, including American, German and Oriental cockroaches, and are also effective against mosquitoes (both Anopheles and Aedes), black flies and carpenter ants, and to some extend against deer ticks. They may be applied to areas, locations and items which are desirably to be kept free of such insects, with applications being direct or of solutions or emulsions thereof, preferably by spraying, or in detergent compositions or other products to be applied to such areas, etc. Because the described neoalkanamides are desirably substantive to surfaces and are usually in liquid state, they give long lasting repellency to such areas, etc., and tests have shown them to be sufficiently long lasting.

14 Claims, 2 Drawing Sheets

N-ARYL AND N-CYCLOAKYL NEOALKANAMIDE INSECT REPELLENTS

This application is a continuation-in-part of my co-pending U.S. Pat. application Ser. No. 07/612,747, filed Nov. 12, 1990, Ser. No. 07/267,141, filed Nov. 4, 1988, now U.S. Pat. No. 5,006,562, Ser. No. 07/609,290, filed Nov. 5, 1990, Ser. No. 07/264,936, filed Oct. 31, 1988, now U.S. Pat. No. 5,015,665, Ser. No. 07/071,305, filed Jul. 16, 1987, now U.S. Pat. No. 4,804,683, and Ser. No. 06/894,985, filed Aug. 8, 1986, now abandoned.

This invention relates to N-monosubstituted neoalkanamides wherein the substituent on the nitrogen is cyclic, such as aryl or cycloalkyl, which are novel chemical compounds that possess significant insect repelling properties. More particularly, this invention relates to such neoalkanamides which are of carbon atom contents in the range of 11 to 14 wherein the neoalkanoyl moiety is of 5 to 8 carbon atoms. The mentioned neoalkanamides, especially N-phenyl neoheptanamide, are effective in repelling insects, such as cockroaches, when applied to areas, locations, items, materials and structures, and to surfaces thereof, to protect them against insect infestation and damage. The present invention also relates to various compositions containing such N-substituted neoalkanamides, which compositions are employed as means for depositing such active compounds onto surfaces to be made repellent to insects, and it also relates to processes of using such compounds and compositions to repel insects.

Although some insects, such as bees, are considered to be useful to man (for plant pollination), many types of insects are classified as pests, and many efforts have been made to eradicate or at least control them. However, although effective poisons have been produced, various insects have developed resistences to them (possibly by "natural selection") and others have been able to detect and avoid poisons. Furthermore, many poisons have undesirable effects on human and other animal life, and therefore uses thereof have often been regulated or forbidden. Some insects, like the common German or house cockroach (*Blattela germanica*), cannot be eliminated entirely from many areas and therefore, realistically, efforts have been made to control them, rather than to eradicate them. Also dead cockroaches left in areas that cannot be reached or cleaned, have been identified as a significant allergen in house dust. Results from recent studies by the National Institutes of Health indicate that 10–15 million people in the United States are allergic to cockroaches. Poisons are ineffective in these situations because dead cockroaches in unreachable areas emit the allergen. An effective repellent is the only feasible means to prevent such allergic reactions and if the repellent is applied to hard-to-reach areas it can minimize the presence of dead insect bodies there. Mosquito repellents have long been marketed and some chemicals that are effective in repelling roaches have been discovered. Such chemicals may be applied to surfaces of walls, floors, cabinets, drawers, packages, containers, rugs, upholstery and carpeting, and in potential nesting places for insects, such as inside walls and between floors. Similarly, when such repellents are of low toxicity they may be applied to the human body and onto pets, zoo animals and livestock. However, some such repellent materials are toxic and others are foul smelling and discoloring, which adverse properties can seriously limit their utilities. Many of the useful insect repellents reported in the literature are teriary amides and of these the one heretofore regarded as the most effective all-purpose insect repellent is N,N-diethyl-m-toluamide, which is often referred to as "DEET". However, the present neoalkanamides are superior to DEET in long lasting effectiveness, e.g., against roaches. Additionally, the invented neoalkanamides are also effective to repel other insects, as well as arachnids, including mosquitoes, black flies, carpenter ants and deer ticks. Except for the N-lower alkyl neoalkanamides described in the previously listed patent applications, of which this application is a continuation-in-part, such as N-methyl neodecanamide and N-methyl neotridecanamide, previously known repellents do not show the same potent and long lasting repellencies. In view of the relatively small number of useful insect repellents known, efforts continue to be made to discover additional repellents which would be of greater repellent actions and of longer lasting effects. Desirably, such compounds also would be of improved physical characteristics, such as of even better aroma, desirable volatility, non-staining character, even lower toxicity, improved stability, greater substantivity to substrates, and repellency against a broader group of insect types.

In accordance with the present invention there are provided insect repellent N-monosubstituted neoalkanamides in which the total number of carbon atoms is in the range of 11 to 14, and is in the range of 12 to 14 when the neoalkanoyl moiety is pivaloyl, and the substituent is a cyclic moiety of at least 5 carbon atoms and for the substituted phenyl moieties is unsubstituted in the ortho position. At present the most preferred of such compounds for employment as an insect repellent, which is especially effective against cockroaches, is N-phenyl neoheptanamide. Also within the bounds of the invention are detergent compositions (both particulate and liquid), carpet and upholstery shampoos, human hair shampoos, hard surface cleaners, and soap and detergent bars comprising such N-substituted aryl and cycloalkyl neoalkanamide(s). Also useful are solutions and dispersions of such neoalkanamide(s) in liquid media or such neoalkanamides dispersed in a particulate or powdered carrier, which liquid or particulate products are suitable for application to an area, location or item from which insects are to be repelled. Also included in the invention are processes for repelling insects by applications of insect repelling amounts of the N-substituted neoalkanamides of this invention to or near a surface, area, location or item from which such insects are to be repelled. In some situations the present repellents may be used in conjunction with insecticides, to repel the insects from one area and toward the location of the insecticide. They may also be formulated with insecticides so that after the repellent effect is lost the treated area will still not be safe for insects. Additionally, compositions containing mixtures of the present repellents with other insect repellents are within the invention, as are mixtures of the invented neoalkanamides.

Computer and manual searches of the prior art have not resulted in the finding of any reports of N-cyclic substituted (such term is considered to be generic to both aryl and cycloalkyl) secondary neoalkanamides of this invention and no analogous N-cyclosubstituted amides were recognized to be useful as insect repellents. Such searches indicated that applicant's N-aryl and N-cycloalkyl neoalkanamides are novel and unobvious.

The closest compounds to such N-cyclosubstituted neoalkanamides of this invention appear to be those described in U.S. Pat. Nos. 4,682,982 and 4,715,862, of Steltenkamp and Camara, in U.S. Pat. No. 4,804,290, and in U.S. patent applications Ser. Nos. 07/612,747, 07/609,290, 07/267,141, 07,264,936 and 06/894,985, all of Steltenkamp, all of which applications have been cited as parents. However, the neoalkanamides described in the first two of the mentioned patents are employed as anti-static agents, not as insect repellents. In Ser. Nos. 07/354,545 and 06/894,983, of Steltenkamp and Eaton, N-lower alkyl neoalkanamides are utilized as components of perfumes. All such patents and applications (and especially those relating to insect repellents) are incorporated herein by reference.

The N-cyclosubstituted secondary neoalkanamides of this invention include those wherein the cyclic substituent is cycloaliphatic or aromatic, and preferably the cyclic moiety is a hydrocarbon (or hydrocarbyl). The neoalkanoyl moiety may be of 5 to 8 carbon atoms and the aryl moiety, including any substituents thereon, which are preferably lower alkyl(s) of 1 to 3 carbon atoms, desirably in meta positions only (with none in the ortho positions and often also with none in the para position, either), will be of 5 to 9 carbon atoms. Among the cyclic substitutents that may be on the amido nitrogen are included cyclopentyl-, alkylcyclopentyl- , cyclohexyl-, alkylcyclohexyl, cycloheptyl- and alkylcycloheptyl. The total number of carbon atoms in the N-substituted neoalkanamide, for good insect repellency, will be in the range of 11 to 14, with the proviso that when the neoalkanoyl moiety is pivaloyl that range is 12 to 14. Of the N-cyclosubstituted neoalkanamides of this invention the substituted neoheptanamides are preferred because they have been shown to be of longer lasting effectiveness in repelling insects from treated surfaces and areas, with N-phenyl neoheptanamide being 90% effective (the standard employed) against cockroaches for at least 25 days, by probit analysis.

The N-cyclosubstituted (or N-cyclic, for short) neoalkanamides may be made from the appropriate neoacids, such as pivalic acid, neohexanoic acid, neoheptanoic acid or neooctanoic acid or appropriate mixtures thereof, or the corresponding acid halides, such as the acid chlorides may be employed. The amides are easily produced by reaction of such acid or acid chloride with the appropriate amine, such as aniline or 3-methyl toluidine. Pure neoalkanamides of the types described may be made but often the commercial or technical grade acids, which may be used, and the amides made from them, will be mixtures.

The invented amides are of the formula

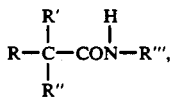

wherein R, R' and R" are alkyl groups, the sum of contents of which is in the range of 3 to 6, and R'" is cyclic (cycloaliphatic or aromatic) of 5 to 9 carbon atoms, and the carbon atoms content of the amide is in the range of 11 to 14, with the provisos that when the neoalkanoyl moiety is pivaloyl the carbon atoms content will be at least 12 and when an aromatic moiety is substituted such substitution will not be in an ortho position and preferably will be in meta poistion(s) only. Further details with respect to R, R' and R" will be given later, in conjunction with a description of neoalkanoic acids which may be employed as starting materials for the production of the neoalkanamides.

Figure 2:
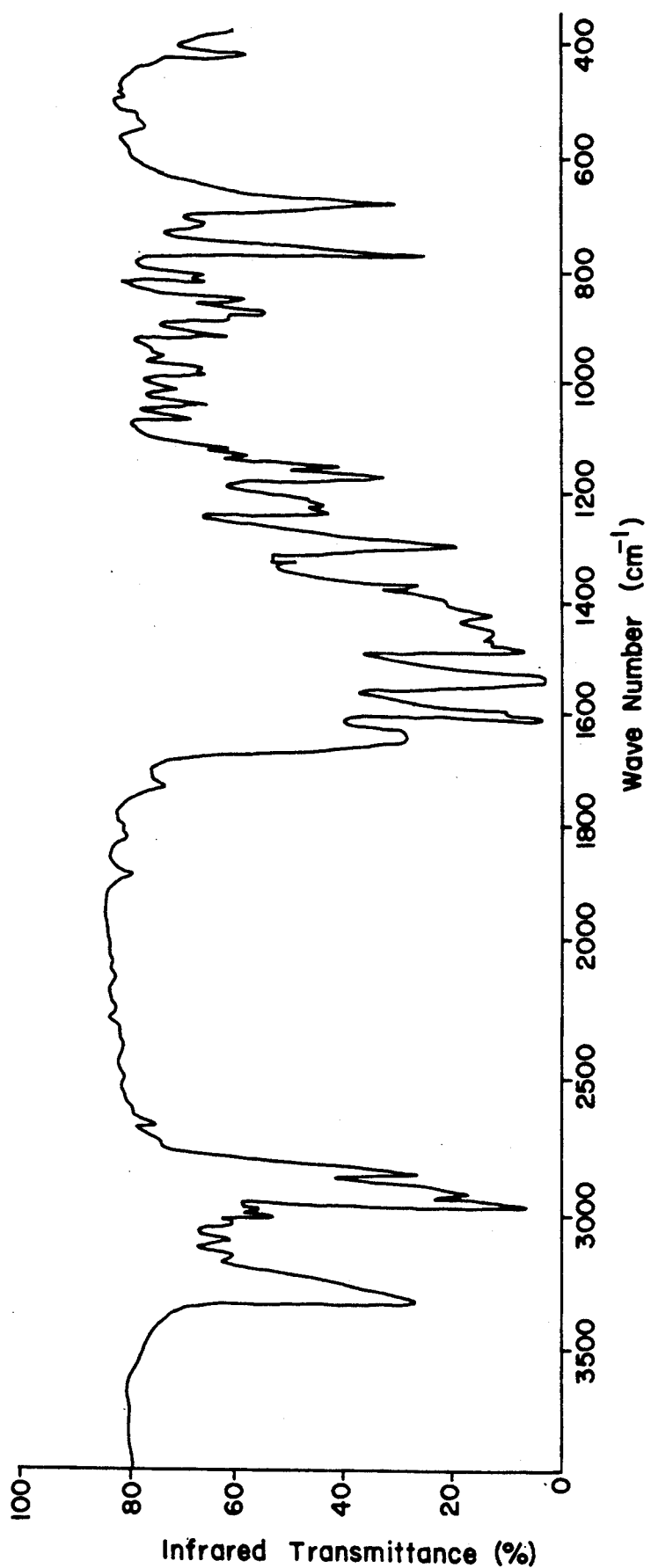

Infrared absorption spectra for some representative and preferred N-cyclosubstituted neoalkanamides of this invention are shown in the drawing, in which:

FIG. 1 is an infrared spectrograph of a sample of N-phenyl neoheptanamide, which is more preferred; and FIG. 2 is an infrared spectrograph of a sample of N-(3-methylphenyl) neoheptanamide.

Both such N-substituted neoalkanamides are considered to be representative of the various other of the N-cyclic neoalkanamide insect repellents of this invention.

To make the neoalkanamides of this invention neoalkanoyl chloride reactant is slowly reacted, with mixing, with the appropriate primary cyclic amine, in a suitable medium, such as ethyl ether, hexane and/or water, producing the amide and hydrochloric acid, and the extent of reaction is monitored by infrared analyses of the reaction mix for presence of the acid chloride. Sodium hydroxide, triethylamine or other material capable of reacting with any hydrochloric acid produced as a result of the reaction that produces the neoalkanamide, may also be present to react with any excess of HCl, and thus drive the reaction. When the neoalkanoyl chloride has been completely consumed mixing is halted and the product is treated with solvent (hexane) and washed with dilute aqueous HCl twice. Then the organic medium, which is about neutral, is separated from the aqueous medium, is then dissolved in the minimum proportion of methanol and is crystallized from it by addition of cold water. The crystals are filtered off and are vacuum dried or they may be recrystallized. The reaction product obtained is water white to light amber in color and is essentially pure. In an alternative method, the neoalkanoic acid may be reacted directly with the lower alkylamine.

Neoalkanoic acids, such as neoheptanoic acid and pivalic acid, are available from Exxon Chemical Americas, and such have been manufactured by reacting a suitable alkene, such as isobutylene or a branched $C_6$, $C_7$ or $C_8$ alkylene feedstock , with carbon monoxide, under high pressure at elevated temperature, in the presence of aqueous acidic catalyst (Koch reaction). The general mechanism involved includes generation of carbonium ion, followed by complexation with carbon monoxide and the catalyst to form a "complex", which is subsequently hydrolyzed to generate the described free acid. The formula of the free neoalkanoic acid is

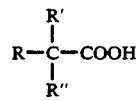

In such neoalkanoic acids and in the neoalkanamides made from them or their acid chlorides R, R' and R" will be methyl in the pivalamides but will include one replacement ethyl for the neohexanamides and a replacement propyl (or isopropyl) or two replacement ethyls for the neoheptanamides. The neooctanamides may include three replacement ethyls or a replacement propyl (or isopropyl) and a replacement ethyl. Neoalkanoic acids mentioned herein and methods for manufacturing them are described in a bulletin entitled NeoAcids Properties, Chemistry and Applications (copyright 1982), Exxon Chemical Americas, hereby incorporated by reference. Acyl chloride starting materials for reactions to produce the invented neoalkanamides may be made from the neoalkanoic acids and suitable chlorating agents, such as phosphorus trichloride, and may be available from Lucidol Division of Pennwalt, Inc. and from White Chemical Corp.

Although it is possible for the insect repellents of this invention to be incorporated in various materials when such materials are being manufactured, as by being mixed in with pulp for making paper, rubber and synthetic organic polymeric plastic batches, and chips for the manufacture of pressed boards, and while the invented insect repellents may also be injected or otherwise inserted into the bodies of items to be made insect repellent, usually the insect repellents will be applied to surfaces of areas, structures or items to be made insect repellent, either by direct application of the insect repelling N-cycloalkyl or aryl neoalkanamide, in liquid solution or dispersion, or dispersed in a powdered carrier, or in a detergent composition, such as a laundry detergent, floor or wall cleaner, upholstery or rug shampoo, hair shampoo, liquid soap, bar soap, or in any other appropriate composition in which it may be usefully incorporated. Among such other appropriate compositions may be mentioned insecticidal and antibacterial washes or dips for humans, pets and farm animals, furniture polishes and finishes, floor waxes and finishes, ointments, salves and topical medicaments, insecticides, fungicides, bactericides, plant fertilizers, mulches and plant potting preparations, to name only a few. In some instances means will be provided for recharging such items and compositions with the active neoalkanamide component to renew the insect repellent effects. In the majority of instances the invented compositions will be applied directly or indirectly by external application to surfaces to be treated, and afterward such application will be made on a continuing basis to maintain a satisfactory degree of insect repellency. Thus, an insect repellent N-cycloalkyl or N-aryl neoalkanamide, such as N-phenyl neoheptanamide, may be painted onto a surface to be treated or it may be applied to such surface by washing it (preferably without subsequent rinsing) with a detergent composition containing the active insect repellent. The invented compounds are usually relatively low melting solids or liquids or a in pasty condition at normal ambient temperatures and are water insoluble, so they tend to be relatively substantive to surfaces from detergent compositions and from other preparations, even if such compositions are rinsed off (although rinsing is often better omitted) and normally, after either direct or indirect application to such surfaces, a sufficient amount of the neoalkanamide should remain to be effectively insect repelling. While different application rates of the different neoalkanamides of this invention are desirably used for effective repelling of different insects from different surfaces under different conditions, it is generally considered that insect repellent effects are obtainable at surface concentrations of the active ingredient in the range of 0.002 to 100 g./sq. m. For economic reasons and for effectiveness against more insects there will normally be applied 0.1 or 0.2 to 10 g./sq. m., preferably 0.5 to 2 g./sq. m., e.g., 1 g./sq. m., when roach repellency is desired. Higher application rates, such as 10 to 100 g./sq. m., can be used against other insects, such as mosquitoes, and sometimes also against roaches.

Because the present insect repellents are sufficiently volatile their presences can be detected by insects in the air near a surface to which they have been applied, although evidence indicates that their efficacies are greatest as contact repellents. Therefore, not only are the surfaces repellent to insects, which will avoid having their body parts contact such surfaces, but the vapors from the N-cyclic neoalkanamides will tend to repel insects from the surrounding space. Thus, the application of the volatile repellent to walls of a china closet can repel roaches from the closet interior thereby preventing them from contacting, soiling and contaminating contained dishes, utensils and silverware. Similarly, coating of pantry surfaces, interior and/or exterior, with a furniture polish containing an invented sufficiently volatile repellent, or use of shelf paper containing such a repellent neoalkanamide can discourage roaches from entering the pantry and contaminating foods contained therein. Also, applying an invented neoalkanamide to clothing or washing clothing with detergent compositions containing an invented repellent may prevent insects from lighting on the clothing and its wearer, and from stinging or biting the wearer. Shampooing of a rug with a rug shampoo or carpet cleaner containing the invented repellent will discourage insects from entering the room and from nesting and laying their eggs in or under the rug. Washing of floors and walls with insect repellent detergent compositions formulated for such purpose, especially such compositions which are not to be rinsed off, will deposit thereon a substantive coating of the invented insect repellent and will discourage insects from contacting the floor and wall surfaces and from entering the treated rooms. It is an important feature of the invented insect repellents that although they are sufficiently volatile to be effective, their repellent properties are persistent because they do not evaporate quickly, often lasting as long as a month or more (even longer if incorporated interiorly in a product). The invented repellents may be formulated with insecticides, such as by being sprayed onto the surfaces of insecticidal powders, e.g., boric acid powder, which is effective against roaches. By use of the neoalkanamide-boric acid composition immediate effectiveness in repelling the roaches is obtained and subsequently, after the repellent activity may have diminished, due to exhaustion by volatilization, any roaches that return to the area may be killed by the insecticide. It is recognized that a more normal practice is to incorporate an attractant with an insecticide but repellent-insecticide compositions also have utility.

It is apparent from the foregoing brief description that the invented insect repellents can be used in many compositions and can be applied in diverse ways. However, among the most useful products which can incorporate the invented neoalkanamides are detergent compositions, from which the neoalkanamides may be surprisingly substantive to the surfaces of washed items. Such detergent compositions operate in several ways to counter insect contamination of the washed item. They remove any earlier contamination, remove stains and soils, on which the insects might feed, and which could attract them, and leave behind the insect repelling neoalkanamide.

The primary component of the present detergent compositions, other than the insect repelling neoalkanamide, is an organic detergent material. Such material may be one of the soaps, preferably a sodium and/or potassium higher ($C_{10-18}$) fatty acid soap, but is preferably a synthetic organic detergent, which may be of a anionic nonionic, amphoteric, ampholytic, zwitterionic or cationic type, or may be a mixture of two or more detergents within one or more of such classifications. Preferably, the detergent will be a synthetic organic detergent of the anionic or nonionic type and often the anionic detergents will be most preferred. Descriptions of many such detergents are found in the well known text *Surface Active Agents and Detergents,* Vol. II, pages 25-138, by Schwartz, Perry and Berch, published in 1958 by Interscience Publishers, Inc. Such compounds are also described in a 1973 publication by John W. McCutcheon, entitled *Detergents and Emulsifiers,* and in subsequent annual issues of such title. Such publications are hereby incorporated by reference.

The anionic detergents employed may be any such suitable detergents (or soaps), but normally will be salts of alkali metals, such as sodium or potassium, or ammonium or lower alkanolammonium salts, e.g., triethanolamine salts. The anionic detergent may be a sulfate, sulfonate, phosphate or phosphonate or salt of other suitable detergent acid but usually will be a sulfate or sulfonate, which together may be designated as "sulf(on)ate". The anionic detergents will include a lipophilic group, which will normally have from 10 to 18 carbon atoms, preferably in linear higher alkyl arrangement, but other lipophilic groups may be present instead, preferably including 12 to 20 carbon atoms, such as branched chain alkyl benzene. In some cases the anionic detergents may include poly-lower alkoxy groups, as in ethoxylated higher fatty alcohol sulfates, e.g., triethoxylated lauryl alcohol sulfate. Normally the number of ethoxy groups in such detergents will be in the range of 1 to 30, preferably 1 to 10. As examples of suitable anionic detergents there may be mentioned: higher fatty alcohol sulfonates, such as sodium tridecyl sulfonate; sodium linear alkyl benzene sulfonates, e.g., sodium linear tridecylbenzene suflonate; olefin sulfonates; paraffin sulfonates; and dioctyl sulfosuccinates. All of the anionic detergents will preferably be sodium salts for most of the particulate detergent compositions of this invention but potassium, ammonium and triethanolammonium salts may be more desirable for some liquid compositions. Usually the detergent will preferably include a lipophilic alkyl moiety of 12 to 16 carbon atoms, often preferably of or averaging 12 to 13 carbon atoms, and preferably such alkyl will be linear.

The suitable nonionic detergents will normally be condensation products of lipophilic compounds or moieties and lower alkylene oxides or polyalkoxy moieties. Highly preferable lipophiles are higher fatty alcohols of 10 to 18 carbon atoms but alkyl phenols, such as octyl and nonyl phenols, may also be used. The alkylene oxide of preference is ethylene oxide and normally from 3 to 30 moles of ethylene oxide will be present per mole of lipophile, but some such alkoxies may be propoxy and/or butoxy and/or isobutoxy.

In preferred embodiemnts of the invented detergent products, the built detergent compositions, in which builders are employed to improve the detergency of the synthetic organic detergent (or soap), there will be present a building proportion of a suitable builder. Builders used may be inorganic or organic, water soluble or water insoluble, or any mixtures thereof. Among such classes of builders may be mentioned water soluble inorganic salts, including: polyphosphates, e.g., sodium tripolyphosphate; carbonates, e.g., sodium carbonate; bicarbonates, e.g., sodium bicarbonate; borates, e.g., borax; and silicates, e.g., sodium silicate; water insoluble inorganic builders, including zeolites, e.g., hydrated Zeolite 4A; and water soluble organic builders, including citrates, gluconates, NTA, and polyacetal carboxylates. In some cases, as when mildness of the product to the human body or to delicate fabrics is important, alkaline builders and other "harsh" builders will be avoided, and in some cases no builders will be present at all.

Various adjuvants may be present in the detergent compositions of this invention to improve various characteristics of such products. Thus, for example, bentonite may be employed as a fabric softener, perfumes and colorants may be added for their aesthetic effects, soil anti-redeposition agents may be employed, such as sodium carboxymethyl cellulose, and solvents or co-solvents may be present, as in liquid compositions. Among other adjuvants there may be mentioned fluorescent brighteners, antistatic agents, antibacterial agents, fungicides, foaming agents, anti-foams, flow promoters, suspending agents, antioxidants, anti-gelling agents, soil release promoting agents, stabilizers and enzymes.

The detergent compositions of this invention may be in particulate, powder, tablet, bar, liquid, paste, gel, capsule, leaf, foam or "aerosol" or other suitable form, as may be best suited for the purpose intended. Methods for manufacturing products in such forms are well known in the art of processing soaps and detergents, and need not be further mentioned here.

While it is possible to apply the present insect repelling N-cycloalkyl and N-aryl neoalkanamides directly to surfaces and items to be made insect repellent, it is often more convenient and also more efficacious to utilize the repellent neoalkanamide as a liquid solution, emulsion or dispersion, or as a particulate or powder product. To make such solutions the neoalkanamide may be dissolved in any suitable solvent, such as a lower alcohol, e.g., ethanol, or an aqueous alcoholic medium. Of course, other solvents may also be employed, such as hydrocarbons, esters, ketones, aldehydes and halogenated hydrocarbons. Among the hydrocarbons and halogenated hydrocarbons there may be mentioned isobutane, other lower hydrocarbons and the chlorofluorinated lower hydrocarbons, such as dichlorodifluoromethane, monofluorotrichloromethane and other chlorofluoro-methanes, -ethanes and -propanes. Such compounds include the liquefiable gases, which can be maintained in liquid state in pressurized dispensing containers, for ready application as sprays or in other suitable forms, to locations which are to be made insect repellent. The invented neoalkanamides may also be in aqueous or other emulsion form, when a suitable emulsifier, hydrotrope or surface active agent is utilized, too. Such neoalkanamides may also be dispersed in particulate or powdered inert or active materials. Among such inert materials may be mentioned silica, calcium carbonate, clay, expanded polystyrene, wood chips and sawdust. Also, the neoalkanamides may be dispersed in active materials, such as detergent composition beads, bentonite (a fabric softener) and boric acid (a roach poison).

Other modes of use of the invented insect repellents, some of which have already been mentioned, include incorporation in materials which are intended for use at or near sites from which the insects are to be excluded. Thus, the repellents may be incorporated in shelf papers, wallpapers, wallpaper glues, rugs and carpeting, and carpet padding. They may be formulated in floor waxes, furniture polishes and other preparations that are intended for applications to surfaces in the areas to be treated. They may be automatically dispensed in certain areas, such as storerooms and warehouses, by timer-operated sprayers or other dispensers, and they may be renewably charged to containers, from which they may be vaporized, such as absorbers and other holders, which may be attached to under sides of garbage can covers or may be concealed in wall mounted "vaporizers".

The detergent compositions of this invention, including those that are useful for washing hard surfaces, such as floors, and also soft surfaces, such as those of carpets, laundry, and human hair, will include an insect repelling proportion of N-cycloalkyl or aryl neoalkanamide or a mixture of such neoalkanamides, which proportion is sufficient so that enough of the neoalkanamide is retained on the washed surface, after washing of it with the detergent composition, to repel insects from such surface, and such detergent composition will also include a detersive proportion of soap or synthetic organic detergent (or any suitable mixture thereof). The neoalkanamide is preferably one wherein the cyclic substituent is aromatic, e.g., phenyl or alkylphenyl, but may also be cyclohexyl, substituted cyclohexyl, cyclopentyl, cylcoheptyl or alkyl or other derivative thereof. As was previously mentioned, the cyclic substituent will be of 5 to 9 carbon atoms and the neoalkanoyl moiety will be of 5 to 8 carbon atoms, with the total carbon atoms content being 11 to 14, except for the pivalamides be trimethyl acetamides), wherein at least 12 carbons should be present. Such carbon atom contents may be those for pure compounds or averages for mixed neoalkanamides.

In particulate built laundry detergent compositions of the invention the active detergent component will usually be synthetic organic detergent selected from the group consisting of anionic, nonionic, amphoteric, ampholytic, and zwitterionic detergents and mixtures thereof, and the builder will be water soluble inorganic or organic builder or water insoluble inorganic builder. The proportions of synthetic organic detergent(s), builder(s), and neoalkanamide(s) to make an effective insect repellent particulate synthetic organic detergent composition will be 1 or 5 to 35%, 10 to 90%, and 0.2 to 10%, respectively. Preferred compositions of such type will have the synthetic organic detergent selected from the group consisting of anionic and nonionic detergents, and mixtures thereof, may contain water soluble filler salt(s), such as sodium sulfate, and will contain a N-aryl or N-cycloalkyl neoheptanamide, such as N-phenyl neoheptanamide or N-(3-methylphenyl) neoheptanamide or a mixture thereof. The proportions of such components for best effects in floor cleaning compositions and other cleaners for hard surfaces will often desirably be 1 to 30% of synthetic organic detergent, 10 to 50% of builder, 0 to 50% of filler and 0.2 to 10% of the repellent.

When liquid detergents containing the invented insect repellent neoalkanamide(s) are made, the same components may be used, plus a liquid medium, but the detergent will preferably be non-soap. Sometimes a conventional emulsifying agent, such as an Emcol®, sold by Witco Chemical Co., Inc., will be employed, in emulsifying proportion. Also, hydrotropes, such as sodium toluene sulfate, and other functional and aesthetic adjuvants, such as have been employed in liquid detergent compositions, and/or fillers, may be included, or not. In the built liquid detergents the synthetic organic detergent content will be in the range of 2 to 25%, the builder content will be in the range of 5 to 40%, the neoalkanamide content will be in the range of 0.2 to 10%, and the liquid medium content, preferably aqueous, will be in the range of 40 to 90%. More preferably, the built liquid detergent compositions of the invention will comprise 3 to 20% of a synthetic organic detergent which is anionic and/or nonionic, 10 to 30% of builder salt(s) for such detergent(s), which may be water soluble, such as potassium pyrophosphate, sodium carbonate, or sodium polyacetal carboxylate, and/or water insoluble, such as sodium zeolite, 0 to 20% of water soluble filler salt, such as sodium sulfate, 0.5 to 5% of one or more of a previously named N-aromatic or cycloalkyl neoheptanamide or other suitable neoalkanamide of the invention, and 50 to 90% of water, preferably deionized water.

When an insect repelling shampoo for use on upholstery, rugs and carpets is to be made, it may comprise 1 to 35%, preferably 5 to 20%, of a detergent selected from the group consisting of water soluble soap(s) and synthetic organic detergent(s), 0 to 40% of builder(s) for the soap and/or detergent, often preferably 0%, and 0.2 to 10% of N-aryl or N-cycloalkyl neoalkanamide, preferably 0.5 to 5%, all being of the types previously mentioned, in a liquid medium, preferably aqueous, the percentage of which may be in the range of 40 to 90%, preferably 70 to 90%, with water being 50 to 90% of the composition, preferably 70 to 90%. Alternatively, the shampoo may be in gel, paste or powder form.

When the present insect repellents are used in shampoos intended for washing human hair on the head and for making the hair repellent of insects, the shampoos will preferably comprise 2 to 25% of soap and/or the previously described synthetic organic detergent(s), and 0.2 to 10% of N-aryl or N-cycloalkyl neoalkanamide, in an aqueous medium, such as 40 to 90% of water, preferably deionized water. The aqueous medium may include up to half thereof of a cosolvent, such as a lower alkanol, e.g., ethanol, or a glycol, but normally the percentage of such cosolvent will be limited to 5 to 20% of the final product. In more preferred embodiments of the shampoos for human hair, there will be present 5 to 22% of synthetic organic detergent, 0 to 20% of water soluble filler salt, 0.5 to 5% of N-aryl or N-cycloalkyl neoalkanamide or mixture thereof, preferably N-phenyl neoheptanamide, N-(3-methylphenyl) neoheptanamide or N-(4-methylphenyl) neoheptanamide (of which the first is most preferred), and 50 to 90% of water, preferably deionized.

Solid or bar or cake insect repellent detergent products can also be made, which may be used for washing persons, animals, laundry, rugs, and/or hard surfaces, such as walls and floors, to make them insect repellent. Such products can comprise "N-cyclic neoalkanamide" (which term will henceforth be used to signify N-aryl neoalkanamides and N-cycloalkyl neoalkanamides) repellent with soap and/or synthetic organic detergent, or may also include builders, fillers and other adjuvants, previously referred to herein. The proportion of N-cyclic neoalkanamide in such products will normally be from 0.2 to 10%, and that of the detersive material will be from 15 to 95%. Such bars will normally be of a moisture content in the range of 2 to 20% and the balance will be of builder(s) and/or filler(s) and/or adjuvant(s), when such are present. Normally, the adjuvant(s) content of the various detergent products will be in the range of 0.5 to 20%, total, with individual adjuvants being in the range of 0.1 to 5%, in most cases.

The various detergent compositions described above may be prepared by processes that are well known in the art and need not be described at length herein. Such processes include spray drying, dry mixing, spray applying and/or coating, agglomerating, sequential dissolving and/or dispersing and/or emulsifying, milling, plodding and pressing.

When the invented insect repellent is to be sprayed or applied in a carrier, such as a liquid or particulate material or medium, the concentration of it therein will be an insect repelling proportion, so that when applied to a surface of a material to be treated (or into the interior or other portion thereof) by spraying, dusting, rubbing, wiping, pouring, depositing or other mechanism, the repellent applied will be in such quantity and/or concentration that it will be effective in repelling insects or a particular type of insect, so that such insect(s) will stay away from the treated location. Such repelling is due to the insect being reluctant to contact the repellent and also in some measure is due to the repellent effect of the vapor from the repellent, which is at least partially volatile, although it may last for as long as a month or more, as normally applied, using the application concentrations that were previously given. The staying power of the repellent may be increased by formulating it with a less volatile carrier, such as a paraffin wax or petrolatum, and when that is done one may find it desirable to increase the amount of the N-cyclic neoalkanamide-present (within the ranges previously recited) to ensure that enough will volatilize to be effectively insect repellent. Also, the repellent lasting power is increased when it is incorporated in the body of an article, such as in a mattress or absorbent sponge, rather than only on a surface that is exposed to the air (and again, one may wish to employ more of the invented repellent in such cases).

The concentration of the repellent chemicals) in a liquid medium, such as an aqueous medium, in which a dispensing agent or emulsifier may be employed, too, will often be in the range of 0.5 to 10%, e.g., about 1% or 5%, for roach repellency. The liquid medium may be water, lower alkanol, such as ethanol, lower ketone, such as acetone, lower hydrocarbon, such as isobutane, cyclopropane or mixture thereof, or halogenated lower hydrocarbon, such as chlorofluorinated, fluorinated or chlorinated lower hydrocarbons, e.g., Propellants 11 and 12. The various "lower" compounds are of 1 to 4 carbon atoms per molecule, preferably 1 or 2 carbon atoms, and in the case of those that are normally in the gaseous state, they are under sufficient pressure to maintain them in liquid state.

Similar concentrations of the invented repellents may be employed in powdered or particulate carriers. Thus, the invented neoalkanamides may be applied, as by spraying of liquid droplets, onto powdered calcium carbonate, silica, clay or boric acid, onto grains of such materials, or onto detergent composition particles or synthetic organic polymer beads (preferably of particle sizes between 125 microns and 2.4 mm. in diameters), in concentrations in the range of 0.2 to 10 or 25%, preferably 0.5 to 5 or 10%, for roach repellents.

In insect repelling processes or treatments in which the invented repellents are employed they will normally be applied to surfaces to be treated at concentrations such that 0.002 to 100 g./sq. m. initially remain on such surfaces after treatment, with such application rate preferably being 0.01, 0.1 or 0.2 to 5 or 10 g./sq. m. and more preferably 0.5 to 2 g./sq. m., e.g., 1 g./sq. m. for most effective and efficient action against roaches. Concentrations outside such ranges may sometimes also be of at least partial effectiveness. When the repellent is in a detergent composition which is employed in an aqueous washing medium, such as water, the wash water will usually contain from 0.05 to 5 or 10% of the detergent composition, but in some applications, such as shampooing of human hair or of carpets or rugs with foam preparations, the concentration may be greater, sometimes being as high as 25%.

When the repellents are incorporated in and applied to surfaces in other media or preparations, such as waxes or furniture polishes, the concentrations thereof will usually be in the same ranges as for detergent compositions, but may be increased, if desired, in some such instances to as high as 25%.

The invented repellents possess various significant advantages over various other repellent materials available. Like the N-lower alkyl neoalkanamides they are essentially non-toxic and therefore are not hazardous to children or pets that might come into contact with them, after application. They are pleasantly aromatic and therefore do not usually adversely affect the aromas of preparations into which they are formulated. They are substantially colorless and therefore can be employed in detergents, shampoos, polishes, sprays, and various compositions and preparations wherein the imparting of color would not be acceptable. They are effective both as contact and vapor repellent and are superior in repelling action to various commercial insect repellents, especially against German cockroaches, which are considered to be the most difficult household insect pest to control. The present repellents are long lasting, with tests having shown some o them, especially N-phenyl neoheptanamide, to be effective to repel roaches for more than three weeks after topical application. They are also considered to be effective repellents against mosquitoes (*Anopheles quadrimaculatus* and *Aedes aegypti*). They are sufficiently stable to be able to maintain their insect repelling properties despite being incorporated in various soap, detergent, polish, wax, insecticide, cosmetic, and coating preparations, in liquid, paste, gel, foam, powder, particulate or solid bar form, or in aqueous or other solvent solutions, emulsions or dispersions, and they are substantive to surfaces to which they are applied from such media.

Experimental work to date has proven conclusively that members of the class of the invented N-cyclic neoalkanamides are superior insect repellents, being especially effective against the common household pest, the German cockroach, and evaluations of such compounds indicate that they will also be effective repellents against other insects, such as those in the group of flies, fleas, lice, mosquitoes, bees, wasps, hornets, ants, beetles and other roaches, such as the American cockroach, and against arachnids, such as spiders, ticks and mites. Because to date data on N-cyclic neoheptanamides are the most complete and are very convincing of the superior insect repelling activity of such N-cyclic neoalkanamides against German cockroaches, and because such data were obtained from controlled tests, conducted in connection with entomological research at a major university, such data will constitute the primary insect repellency results that will be reported in the examples given below.

The following examples illustrate but do not limit the invention. Unless otherwise stated, all parts are by weight and all temperatures are in ° C.

EXAMPLE 1

N-(3-methylphenyl) neoheptanamide was made from m-toluidine and neoheptanoyl chloride (which can be made by chlorinating neoheptanoic acid with $PCl_3$) in a reaction conducted in a glass flask equipped with a stirrer, a thermometer and an addition funnel (a dropping funnel), and connected to a condenser equipped with a Drierite ® desiccant tube. The flask was placed in an ice bath and was charged with 90.8 grams of m-toluidine, and 85.7 grams of triethyl amine (which functioned to remove from the reaction mixture any HCl that was produced). Then 109.8 grams of neoheptanoyl chloride (obtainable from Pennwalt's Lucidol Div.) were added dropwise to the flask, while mixing was continued, with intermediate additions of 300 ml. portions of distilled water (after 30 minutes) and hexane (after an additional five minutes). Samples were analyzed for acid chloride content by infrared absorption analysis and the reaction was considered complete and mixing was discontinued after 75 minutes, when all the neoheptanoyl chloride had been added and no acid chloride remained in the mix. After such completion of the reaction the flask contents were allowed to come to room temperature. The mixture was then transferred to a 6-liter separatory funnel with the aid of another 300 ml. of hexane and was washed twice with dilute aqueous HCl to a pH of 6.5, to separate the N-(3-methylphenyl) neoheptanamide from the triethyl amine chloride, after which the hexane layer was drawn off and the solvent was evaporated off. The resulting product was then dissolved in 300 ml. of methanol (about the minimum amount needed for solution) and two liters of cold distilled water were added to such solution, with stirring, which resulted in precipitation of solid N-(3-methylphenyl) neoheptanamide. Such was filtered out from the accompanying liquid and was dried under vacuum. The resulting product was obtained in 68% yield. After recrystallization it was found to have a melting point of 62°-64° C. Its infrared transmission spectrum is shown in FIG. 2.

N-phenyl neoheptanamide, of a melting point of 64.65° C., made in the same manner as described above, with the only changes in the procedure being in the use of 0.85 g. mole of aniline (79 g.) instead of 0.85 g. mole (90.8 g.) of m-toluidine. The product, N-phenyl neoheptanamide, is obtainable in about 70% yield (it is expected that yields will approach 90% as the process is improved further), with the product being at least 95% pure (99% purity is obtainable, but is not usually cost efficient), like the purity of N-(3-methylphenyl) neoheptanamide, the making of which was described above. The product's infrared spectrograph is shown in FIG. 1.

In reactions like the neoheptanoyl chloride reactions described above in this example other N-cyclic neoalkanamides of this invention are made, including N-phenyl neohexanamide, N-phenyl neooctanamide, N-cyclohexyl neohexanamide, N-cyclohexyl neoheptanamide, N-(3,5-dimethyl) cyclohexyl pivalamide, N-(3-methylphenyl) pivalamide, N-(3-methylphenyl) neoheptanamide, N-(3-ethylphenyl pivalamide, and N-(3,5-dimethylphenyl) pivalamide, using equivalent gram-molar weights of the appropriate cyclic substituted primary amines, triethyl amine and neoalkanoyl chlorides. The products are obtained in essentially the same types of yields and of essentially the same purity as the N-phenyl neoheptanamide and N-(3-methylphenyl) neoheptanamide previously described.

EXAMPLE 2

The compounds for which manufacturing methods are described in Example 1 are made but the starting materials which act as sources of the neoalkanoyl moieties are the corresponding neoalkanoic acids instead of the acid chlorides, and no triethyl amine is employed. In such reactions, in which the neoalkanoic acids are reacted with about a 10% excess, over stoichiometric proportion, of the cyclic substituted amines the reaction is desirably conducted in a closed system and the flask is equipped with a heating mantle, a magnetic stirrer, a source of nitrogen gas with means for conveying it to below the surface of the reaction mixture, and a thermometer and thermostatic control to regulate the temperature of the reaction mixture, which is held at about 240° C. for about five hours. The reaction products are separated and washed and have solvent removed from them in the same manner as described in Example 1. The products resulting are of infrared spectrographs like those of samples of the corresponding products of Example 1.

EXAMPLE 3

The N-(3-methylphenyl neoheptanamide made by the "neoheptanoyl chloride" process of Example 1 was tested for cockroach repellency, using 50 male German cockroaches in the test, which is a modification of the method described by Goodhue and Tissol in J. Econ. Entomol. 45:133-134 (1952). In such modified method two ml. of a 1% solution of the N-(3-methylphenyl) neoheptanamide were applied to the entire inside surface (188 sq. cm.) of an unwaxed 237 ml. Dixie ® ice cream carton, with two 1.5 cm. diameter holes cut in opposite sides of the cup, at the lip, which deposited approximately 1 g./sq. meter of the N-cyclic neoalkanamide. Control cups were treated with acetone only and both cups were dried in a fume hood for an hour. Both the experimental and control cups were placed at opposite sides of plastic test cages (51×28×20 cm.) to which the roaches had been acclimated by a previous 2-day occupancy. Food and water were available to the roaches between the cups. The side walls of the containers were coated with a Teflon ® emulsion to prevent the roaches from climbing them. The test site was kept on an alternating 12 hours light—12 hours dark cycle at 27° C. and midway through each photophase the numbers of roaches resting on the inner walls of each cup were recorded, after which the insects were disturbed and the positions of the cups were reversed. The test continued for 25 days or until an equal number of roaches was found in both cups. By probit analysis the number of days of 90% effectiveness (9 times as many of the roaches in the untreated cup as in the treated cup), which is considered to be a standard for successful repellency, was determined. The more days of 90% or more repellency the better the insect repellent. By this test N-(3-methylphenyl) neoheptanamide was rated over 25 (days 90% or more effectiveness) against male German cockroaches (*Blatella germanica*). Similar results were also noted for N-phenyl neoheptaanamide, with the rating for it being 24.8. Both such N-cyclic neoalkanamides are also repellent of American cockroaches and various other insects and arachnids, including mosquitoes, black flies, carpenter ants and deer ticks. It should be noted that in another testing of N-(3-methylphenyl) neoheptanamide for insect repellency the rating thereof Was less than 25 days, so the N-phenyl neoheptanamide may be considered to be the more effective of these repellents.

The other N-cyclic neoalkanamides mentioned in Examples 1 and 2 are also repellent of cockroaches, as can be shown by the laboratory test described. What is even more important is that they are all insect repellents, which is surprising, because all the N-substituted neoalkanamides previously known to be insect repellents were not cyclic or aromatic in structure and it had been thought that they had to be in liquid state under ambient conditions, to be insect repellent. Furthermore, it is surprising that the present N-cyclic neoalkanamides, in rather narrow total carbon atom content ranges and of certain molecular structures, are effective, while outside such ranges and of different structures (ortho-substituted) aryls are not repellent.

In the described tests results are the same whether the repellents are made by the direct condensation method, from neoalkanoic acids or from neoalkanoyl chlorides.

Instead of applying the repellents to the test surfaces in acetone solution they may be sprayed onto such surfaces by means of "aerosol" or pressurized sprays in a 50:50 mixture of isobutane and cyclobutane or a 60:40 mixture of Freon 12 and Freon 11 (dichloridifluoromethane and trichloromonofluoromethane, respectively) or in other pressurized solvents. Instead of applying the solutions as 1% solutions, as in the tests reported earlier in this example, concentrations in the range of 0.5 to 30% may often be used, depending to some extent on the solubility of the repellents in the solvent system employed, for example,15% in the Freon system, 20% in the hydrocarbon system, 5% in ethanol, and 25% in methyl ethyl ketone. Aqueous systems may also be used, preferably with emulsifiers or suitable surface active agents being present to hold the repellent in homogeneous suspension as colloidal droplets, with its concentration usually being somewhat lower than for the organic solvent solutions, e.g., 3%, 5% and 7%. All such liquid systems may be applied with the aids of cloths, pads, spray cans and nozzles, or gels or pastes can also be used, and applications may be to test surfaces or to actual areas, locations and items from which insects and arachnids are to be repelled.

In practical tests, on actual kitchen floors, counters, drainboards and walls, and in kitchen cabinets and dishwashers, and under refrigerators, in roach-infested apartments, significantly fewer roaches will be observed on surfaces to which or near which the invented repellents are applied than on control surfaces, and fewer roaches are found on the bottoms and shelves of cabinets and pantries when walls thereof are treated with the invented repellents, especially when the repellent is N-phenyl neoheptanamide, N-(3-methylphenyl) heptanamide or a 50:50 mixture thereof, indicating that the repellents are vapor-effective too, as well as contact-effective. When floors, walls, counters, sinks, cabinets, appliances, windows, doors, rugs and carpets in a house or apartment are treated with preferred embodiments of the invented repellents, e.g., N-phenyl neoheptanamide and/or N-(3-methylphenyl) neoheptanamide, the incidence of cockroach infestation is reduced, compared to control apartments where no repellent is applied. However, because of the initial presence of the pests in the premises, control of them may take as long as a week, a month or more, and sometimes can require several applications of the repellent. In some instances the application rates are desirably increased to as high as 10 g./sq. m. but in other instances such rates may be dropped to 0.01 g./sq. m. or lower. Of course, results are usually better with the higher application rates.

EXAMPLE 4

N-(3-methylphenyl) neoheptanamide, dissolved at a suitable concentration, e.g., 10%, in acetone, is applied to a cotton stocking so that 1 g./ of the neoalkanamide is on 280 sq. cm. of stocking. Two hours after treatment of the stocking (during which period the acetone volatilizes off) the stocking is pulled over a previously installed nylon stocking on the arm of a human test subject and that so-covered arm is inserted into a cage of adult mosquitoes of a type against which DEET is an effective repellent. Two such species are *Aedes aegypti* and *Anopheles quadrimaculatus*. If fewer than five mosquitoes bite the subject through the stocking during a one-minute exposure the test is repeated 24 hours later, and if fewer than five mosquitoes then bite the subject the test is repeated weekly thereafter until five bites are received within a one-minute exposure period. The degree of repellency of a treatment chemical or composition is measured by the number of days from application of the chemical to the stocking until five mosquitoes bite the test arm within the one-minute exposure period. The described test is an Agricultural Research Service (U.S.D.A.) screening test and is that which is employed by the U.S.D.A. Insects Affecting Man and Animals Research Laboratory, at Gainesville Fla.

In the described test against *Aedes aegypti* DEET is rated 22 and N-methyl neodecanamide (MNDA), a standard for N-lower alkyl neoalkanamides, is rated 15, and when the test mosquito is *Anopheles quadrimaculatus* the ratings are 29 and 36, respectively. The present N-cyclic neoalkanamides such as N-phenyl neoheptanamide and N-(3-methylphenyl) neoheptanamide, are considered to be about equivalent to the DEET and MNDA standards, in mosquito repellency, as may be measured by the described test.

in actual use on the human body, to which they are applied, dissolved in a suitable solvent, in a skin lotion or cream, or in an "aerosol" spray, the N-cyclic neoheptanamides will be about equivalent to DEET, giving at least an hour's protection against *Aedes aegypti* and *Anopheles quadrimaculatus* when 0.3 g. is applied to a human forearm. Similar results are obtainable with other N-cyclic neoalkanamides of the type described in Examples 1 and 2.

EXAMPLE 5 (Built Particulate Detergent)

| EXAMPLE 5 (Built Particulate Detergent) | |
| --- | --- |
| Component | Percent |
| Sodium linear tridecyl benzene sulfonate | 20.0 |
| Sodium tripolyphosphate | 40.0 |
| Sodium carbonate | 10.0 |
| Sodium bicarbonate | 10.0 |
| Borax | 5.0 |
| Enzyme blend (proteolytic + amylolytic in powdered carrier) | 1.0 |
| Sodium carboxymethylcellulose | 0.5 |
| Fluorescent brightener | 1.0 |
| N-(3-methylphenyl) neoheptanamide | 2.0 |
| Water | 10.5 |
| | 100.0 |

All of the components of the detergent composition except the enzyme powder and repellent are mixed together in a crutcher slurry, which is spray dried to hollow globular bead form, of particle sizes in the range of No's. 10 to 100, U.S. Sieve Series. Subsequently, the enzyme powder is blended with the spray dried beads and the melted insect repellent is sprayed onto the mixture, while it is being tumbled, to form a uniform composition. In place of the N-(3-methylphenyl) neoheptanamide there may be substituted N-phenyl neoheptanamide or others of the previously mentioned N-cyclic neoalkanamides of this invention and an insect repellent detergent composition will result, which can impart insect repellent properties to washed laundry. Also, the proportion of the active insect repellent may be increased to 4%, for example, to improve such insect repellency.

EXAMPLE 6 (Floor Cleaner)

| EXAMPLE 6 (Floor Cleaner) | |
|---|---|
| Component | Percent |
| Sodium linear $C_{12-14}$ alkylbenzene sulfonate | 10.0 |
| Sodium tripolyphosphate | 40.0 |
| Sodium carbonate | 20.0 |
| Sodium sulfate, anhydrous | 27.0 |
| N-phenyl neoheptanamide | 3.0 |
| | 100.0 |

The detergent, builder and filler powders are mixed together and the N-phenyl neoheptanamide, in melted state, is sprayed onto the powder mix while mixing is continued.

The resulting powder is dissolved in water and is used to wash linoleum, vinyl tile and ceramic tile floors in areas of homes wherein German or American cockroaches had been seen. After repeated washings, without rinsing, over a period of a month, sightings of the roaches are significantly fewer is almost all cases and many times none are seen. However, if such treatment is discontinued the roaches are often seen again. Also, when the cleaner is rinsed off the floor some repellency can be noted, but it is at a reduced level. Similar results are obtainable when the N-phenyl neoheptanamide is replaced in the cleaner formula by N-(3-methylphenyl) neoheptanamide or is used in mixture with it or with N-methyl neodecanamide, using about equal proportions of each such repellent. Also, similar results are obtainable when others of the cyclic neoalkanamides of the invention are employed and when the amounts thereof present are varied within the describe range, 0.2 to 10%, so that the amount of the insect repellent applied to the surface treated is in the range of 0.002 to 100 g./sq. m., preferably being in the range of 0.2 to 10 g./sq. m.

EXAMPLE 7 (Scouring Cleanser)

| EXAMPLE 7 (Scouring Cleanser) | |
|---|---|
| Component | Percent |
| Silex (finely divided silica powder) | 97.5 |
| Sodium linear dodecyl benzene sulfonate | 2.0 |
| N-phenyl neoheptanamide | 0.5 |
| | 100.0 |

EXAMPLE 8 (Build Liquid All-Purpose Detergent)

| EXAMPLE 8 (Built Liquid All-Purpose Detergent) | |
|---|---|
| Component | Percent |
| *Nonionic detergent | 1.0 |
| Sodium linear dodecyl benzene sulfonate | 2.0 |
| Sodium cumene sulfonate | 5.0 |
| Sodium carbonate | 5.0 |
| Sodium bicarbonate | 1.0 |
| Fluorescent brightener | 0.02 |
| Dye | 0.01 |
| N-phenyl neoheptanamide and/or N-(3-methylphenyl) neoheptanamide | 1.0 |
| Water (deionized) | 84.97 |
| | 100.0 |

*Condensation product of 1 mole of higher fatty alcohol mixture averaging 10 carbon atoms, with 5 moles of ethylene oxide.

EXAMPLE 9 (Carpet Cleaner)

| EXAMPLE 9 (Carpet Cleaner) | |
|---|---|
| Component | Percent |
| Sodium salt of lauric monoethanolamide sulfosuccinate | 30.0 |
| Mixed lipolytic, proteolytic and amylolytic enzymes | 2.0 |
| Sodium tripolyphosphate | 20.0 |
| Sodium hexametaphosphate | 5.0 |
| Sodium monophosphate | 3.5 |
| Sodium bicarbonate | 20.0 |
| Urea | 8.0 |
| *Micro-Cel ® | 10.0 |
| N-phenyl neoheptanamide | 1.5 |
| | 100.0 |

*Finely divided hydrated synthetic calcium silicate (Johns-Manville Products Corp.)

This product should be diluted 1:30 with water before use. One hundred grams will suffice to clean about ten square meters of soiled carpeting.

EXAMPLE 10 (Upholstery Cleaner)

| EXAMPLE 10 (Upholstery Cleaner) | |
|---|---|
| Component | Percent |
| *Sulframin OBS | 10.0 |
| Aqueous ammonia (28%) | 30.0 |
| Water | 58.5 |
| N-phenyl neoheptanamide | 1.5 |
| | 100.0 |

*Linear alkylaryl sulfonic acid (Witco Chemical Corp.)

Before use this upholstery cleaner is mixed 1:3, by volume, with Stoddard solvent.

EXAMPLE 11 (Hair Shampoo)

| EXAMPLE 11 (Hair Shampoo) | |
|---|---|
| Component | Percent |
| Ammonium monoglyceride sulfate | 22.0 |
| Hydroxypropyl methyl cellulose | 1.0 |
| Polyacrylamide | 1.0 |
| N-phenyl neoheptanamide | 1.0 |
| Deionized water | 75.0 |
| | 100.0 |

EXAMPLE 12 (Skin Cream)

| EXAMPLE 12 (Skin Cream) | |
|---|---|
| Component | Amount (as indicated) |
| Yellow ceresin wax | 2.0 ounces |
| Yellow beeswax | 2.0 ounces |
| Stearic acid | 2.0 ounces |
| White petrolatum | 4.0 ounces |
| White mineral oil | 8.0 fluid ounces |
| Water | 6.0 fluid ounces |
| Borax | 0.3 ounce |
| Triethanolamine | 0.5 fluid ounce |

The ceresin, beeswax, petrolatum, stearic acid and white mineral oil are melted together by heating to 71° C. The borax is dissolved in hot water and the triethanolamine is added to the solution, with the temperature being raised to 71° C. The aqueous solution is poured into the melted wax mixture with stirring and stirring is continued as the mixture is removed from the heat. When it begins to thicken there are added to it 10 grams of N-phenyl neoheptanamide or N-(3-methylphenyl) neoheptanamide or 5 grams of each of such neoalkanamides.

EXAMPLE 13 (Body Lotion)

| EXAMPLE 13 (Body Lotion) | |
|---|---|
| Component | Parts |
| Glyceryl monostearate | 50.0 |
| Oleic acid | 30.0 |
| Mineral oil | 15.0 |
| Lanolin | 10.0 |
| Triethanolamine | 12.0 |
| Sodium lauryl sulfate | 10.0 |
| Preservative | 10.0 |
| Water (deionized) | 980.0 |
| N-phenyl neoheptanamide | 12.0 |

EXAMPLE 14 (Bar Soap)

| EXAMPLE 14 (Bar Soap) | |
|---|---|
| Component | Percent |
| *Higher fatty acid soap chips | 88.0 |
| N-phenyl neoheptanamide | 1.0 |
| Titanium dioxide | 1.0 |
| Preservative (stannic chloride) | 0.2 |
| Water | 9.8 |
| | 100.0 |

*80:20 tallow:coco sodium soap

Instead of soap bars and cakes, soap-synthetic bars can be made by substituting sodium coco-monoglyceride sulfate for up to 25% of the soap content of formula. Similarly, by employing a suitable plasticizer, all-synthetic detergent bars can be made.

Preservative, titanium dioxide, repellent and some water are milled with the dried soap chips (which contain about 8% water), the product resulting in plodded and the bar made is cut to lengths and pressed to cake shape. Laundry bars can be made by adding 20 to 40% of builder salt, such as sodium tripolyphosphate and/or sodium carbonate to the formula, usually with an increase in the moisture content to improve plasticity during processing. Framed laundry bars and synthetic laundry bars can also be made and the content of the insect repellent will sometimes be increased in such bars, up to about 5%.

EXAMPLE 15 (Repellent Spray)

| EXAMPLE 15 (Repellent Spray) | |
|---|---|
| Component | Percent |
| *Propellant 12 | 45.5 |
| *Propellant 11 | 45.5 |
| Mineral oil | 4.0 |
| N-phenyl neoheptanamide | 5.0 |
| | 100.0 |

*dichlorodifluoromethane
*trichloromonofluoromethane

The mineral oil and insect repellent are dissolved in the pressurized propellant mixture and such mixture is pressure filled into a dispensing container equipped with a spray nozzle designed for optimum spraying of the repellent solution.

EXAMPLE 16 (Powdered Repellent)

| EXAMPLE 16 (Powdered Repellent) | |
|---|---|
| Component | Percent |
| Clay, powdered | 99.0 |
| N-(4-methylphenyl) neoheptanamide | 1.0 |
| | 100.0 |

EXAMPLE 17 (Floor Wax)

| EXAMPLE 17 (Floor Wax) | |
|---|---|
| Component | Percent |
| Montan based ester wax | 6.0 |
| Polyethylene wax | 4.0 |
| Non-oxidized microcrystalline wax | 5.0 |
| Tall oil fatty acids | 0.2 |
| Aqueous potassium hydroxide solution (43%) | 0.5 |
| N,N-diethylaminoethanol | 1.0 |
| Methyl carbitol | 1.0 |
| N-cyclohexyl neooctanamide | 2.0 |
| Water | 80.3 |
| | 100.0 |

EXAMPLE 18 (Aerosol Furniture Polish)

| EXAMPLE 18 (Aerosol Furniture Polish) | |
|---|---|
| Component | Parts |
| Carnauba wax | 5.0 |
| Beeswax | 5.0 |
| Ceresin wax | 5.0 |
| Silicone oil (DC 200) | 5.0 |
| Stoddard solvent | 40.0 |
| Sodium soap (75:25 tallow:coco) | 2.0 |
| Water | 130.0 |

A wax-silicone concentrate is made by heating the Stoddard solvent to a temperature of about 52° C. and gradually adding to it the pre-melted waxes and silicone oil with agitation. Concurrently, the soap is dissolved in the water at a temperature of about 90° C., after which the hot soap solution is admixed with the wax dispersion, under vigorous agitation. The mixture is then cooled rapidly to room temperature and 385 parts of water, 71 parts of naphtha and 15 parts of N-(3,5-dimethylphenyl) pivalamide (dissolved in the naphtha) are slowly added to it. 71 Parts of Propellent 12 are then pressure loaded into dispensing containers after pre-loading of the balance of the composition.

EXAMPLE 19 (Shelf Paper)

Rolls of shelf paper are sprayed on both sides thereof with N-(3-methylphenyl) neohexanamide, dissolved in a volatile solvent (acetone) and are re-rolled after volatilization off of the solvent. The proportion of repellent is regulated to be about 2%, although in some instances as little as 0.1% may be employed. The shelf paper has a long "shelf life" prior to use because loss of the repellent by volatilization is inhibited by the rolling of the paper. In a modification of this example the N-cyclic neoalkanamide repellent is added to the paper pulp during the manufacturing process but care must be taken not to drive off the repellent during any drying operations.

EXAMPLE 20 (Garbage Can Insect Repellent)

A 2% concentration of N-(3-methylcyclohexyl) neohexanamide in a sponge is made by injecting the N-cyclic neoalkanamide into the interior of an open celled polyurethane form, of flat cylindrical shape, which is inserted in a perforated holder affixed to the interior of the lid of a "step-on" kitchen waste container.

EXAMPLE 21 (Repellent-Insecticide)

| EXAMPLE 21 (Repellent-Insecticide) | |
| --- | --- |
| Component | Percent |
| Boric acid | 98.0 |
| N-phenyl neoheptanamide | 2.0 |
| | 100.0 |

The various products of Examples 5–21 are all effective in repelling insects, especially German and American cockroaches. However, they represent only a few of the many compositions and articles of manufacture within the present invention.

The invention described herein is a significant one because mankind has long been in need of effective insect repellents and such compounds have been comparatively rare. Also, among the invented compounds are several which are as effective as or more effective than the previously known best commercial repellents. The invention is unobvious because the art prior to this invention and those of the mentioned parent applications did not teach that secondary neoalkanamides would be insect repellents of long lasting effects. Neither does any art teach any equivalence or interchangeability of aromatic or cyclic substituents on such amide nitrogen for insect repellency. In fact, applicant has discovered that such equivalency does not exist, except for some types of compounds. Note that while it is important that the total number of carbon atoms in the insect repellent secondary amide of this invention should be in the range of 11 to 14, even 11-carbon compounds are ineffective if the neoalkanoyl moiety is pivaloyl. If substituents on the ring of the cyclic compound are in ortho position(s), as in N-(2-methylphenyl) neoheptanamide, the compound will be ineffective as a longer lasting insect repellent. Also, while the inventor previously thought that to be effective insect repellents his secondary amides should normally be in liquid state, he has now discovered some normally solid secondary amides that are usefully effective. In short, except for rather closely related compounds of the types described by applicant, it appears that the insect repellency of his described N-cyclic neoalkanamides wasn't generally predictable and hence his described discoveries are unobvious.

The invention has been described with respect to various illustrations and embodiments thereof but is not to be limited to them because it is evident that one of skill in the art will be able to utilize substitutes and equivalents without departing from the invention.

What is claimed is:

1. A process for repelling insects from an area, location or item which comprises applying to or near such an area, location or item an insect repelling quantity of an insect repellent N-monosubstituted amide which is an substituted or unsubstituted aryl or cycloalkyl neoalkanamide in which the total number of carbon atoms is in the range of 11 to 14 and is in the range of 12 to 14 when the neoalkanoyl moiety is pivaloyl, and the substituent on the nitrogen of the amide is aryl or cycloalkyl moiety of at least 5 carbon atoms in which the aryl is unsubstituted in the ortho positions thereof.

2. A process according to claim 1 wherein the neoalkanamide is one in which the substituent on the nitrogen is an aryl of 6 to 9 carbon atoms and the neoalkanoyl moiety is of 5 to 8 carbon atoms.

3. A process according to claim 2 wherein the substituent on the nitrogen of the neoalkanamide is phenyl or alkylphenyl and the neoalkanoyl moiety is of 5 or 7 carbon atoms.

4. A process according to claim 3 wherein the substituent on the nitrogen of the neoalkanamide is phenyl.

5. A process according to claim 4 wherein the neoalkanamide is N-phenyl neoheptanamide.

6. A process according to claim 3 wherein the neoalkanamide is N-(3-methylphenyl) neoheptanamide or N-(4-methylphenyl) neoheptanamide.

7. A process according to claim 1 wherein the application rate of the neoalkanamide is in the range of 0.01 to 5 g./sq. m 8. A process according to claim 3 wherein the application rate of the neoalkanamide is in the range of 0.5 to 2 g./sq. m.

9. A process according to claim 1 wherein the N-monosubstituted neoalkanamide is applied to the area, location or item in or with a detergent composition which comprises a detersive proportion of soap or synthetic organic detergent, and the proportion of such neoalkanamide so applied is sufficient so that enough is retained on the washed area, location or item, after washing such with the detergent composition applied, so that insects are repelled from such area, location or item.

10. A process according to claim 9 wherein the neoalkanamide is one in which the substituent on the nitrogen thereof is phenyl or alkylphenyl and the neoalkanoyl moiety is of 5 or 7 carbon atoms.

11. A process according to claim 10 wherein the neoalkanamide is N-phenyl neoheptanamide.

12. A process according to claim 10 wherein the neoalkanamide is N-(3-methylphenyl) neoheptanamide or N-(4-methylphenyl) neoheptanamide.

13. A process according to claim 9 wherein the detergent composition is a floor cleaner which comprises 1 to 30% of a detergent of the group of water soluble soaps and water soluble synthetic organic detergent(s) selected from the group consisting of anionic, nonionic, amphoteric, ampholytic and zwitterionic detergents and mixtures thereof, 0.2 to 10% of such neoalkanamide or a mixture of such neoalkanamides, and 10 to 50% of builder(s) for the detergent(s) and 0 to 50% of filler(s) and/or diluent(s), and the floor cleaner is applied to the floor, in an aqueous medium and the floor is cleaned with such floor cleaner, with the rate of application being such that an insect repellent amount of the neoalkanamide is retained on the floor after completion of cleaning and insects are repelled from the floor.

14. A process according to claim 9 wherein the detergent composition is a rug shampoo for cleaning rugs and carpets and for making them repellent of insects, which rug shampoo comprises 1 to 35% of a detergent which is a soap or a synthetic organic detergent, 0.2 to 10% of such neoalkanamide and 0 to 40% of a builder, in a liquid medium, and the rug cleaner is applied to the rug or carpet and the rug is cleaned with it, with the rate of application of the rug cleaner being such that the rug or carpet retains an insect repellent amount of the neoalkanamide and insects are repelled from it.

* * * * *